United States Patent
Good et al.

(10) Patent No.: US 9,682,189 B2
(45) Date of Patent: Jun. 20, 2017

(54) SMART CHECK VALVE

(71) Applicant: CareFusion 2200, Inc., San Diego, CA (US)

(72) Inventors: Lee Good, San Diego, CA (US); Corey Michael Magers, Oceanside, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 14/634,596

(22) Filed: Feb. 27, 2015

(65) Prior Publication Data

US 2016/0250413 A1    Sep. 1, 2016

(51) Int. Cl.
| | | |
|---|---|---|
| *A61M 5/168* | (2006.01) |
| *A61M 39/10* | (2006.01) |
| *F16K 11/02* | (2006.01) |
| *F16K 27/02* | (2006.01) |
| *A61M 39/24* | (2006.01) |
| *A61M 5/142* | (2006.01) |
| *F16K 15/14* | (2006.01) |

(52) U.S. Cl.
CPC ........ *A61M 5/16881* (2013.01); *A61M 5/142* (2013.01); *A61M 39/10* (2013.01); *A61M 39/24* (2013.01); *F16K 11/022* (2013.01); *F16K 15/147* (2013.01); *F16K 27/0263* (2013.01); *A61M 2039/1083* (2013.01); *A61M 2039/1088* (2013.01); *A61M 2039/2433* (2013.01)

(58) Field of Classification Search
CPC .. A61M 5/16881; A61M 5/142; A61M 39/10; A61M 39/24; F16K 11/052; F16K 11/022; F16K 27/0263; Y10T 137/7891
See application file for complete search history.

(56) References Cited

U.S. PATENT DOCUMENTS

| | | | | |
|---|---|---|---|---|
| 4,915,687 A | * | 4/1990 | Sivert | A61M 39/02 137/605 |
| 4,954,130 A | * | 9/1990 | Edwards | A61M 39/02 604/167.02 |
| 5,006,114 A | * | 4/1991 | Rogers | A61M 39/26 604/245 |

(Continued)

*Primary Examiner* — Craig Schneider
*Assistant Examiner* — Kevin Barss
(74) *Attorney, Agent, or Firm* — McDermott Will & Emery LLP

(57) ABSTRACT

A connector valve for use with an infusion set. The connector valve includes a body defining a chamber. The body includes a primary inlet, a secondary inlet, and an outlet. The connector valve includes a compressible member within the chamber that compresses from an uncompressed state to a compressed state. The connector valve includes a resilient member within the chamber that engages with the compressible member. The resilient member moves from an open configuration when the compressible member is in the uncompressed state to an occluding configuration when the compressible member is in the compressed state. The resilient member in the open configuration permits a bidirectional primary fluid flow between the primary inlet and the outlet, and the resilient member in the occluding configuration permits a bidirectional secondary fluid flow between the secondary inlet and the outlet, and unidirectional primary fluid flow from the primary inlet to the outlet.

28 Claims, 2 Drawing Sheets

(56) References Cited

U.S. PATENT DOCUMENTS

| | | | | |
|---|---|---|---|---|
| 5,095,765 A | * | 3/1992 | Filbey | G01N 1/2035 73/863.86 |
| 5,125,903 A | * | 6/1992 | McLaughlin | A61M 39/0606 137/849 |
| 5,147,333 A | * | 9/1992 | Raines | A61M 39/02 137/625.34 |
| 5,676,346 A | | 10/1997 | Leinsing | |
| 5,699,821 A | | 12/1997 | Paradis | |
| 5,810,768 A | * | 9/1998 | Lopez | A61M 39/02 600/573 |
| 5,911,710 A | * | 6/1999 | Barry | A61M 39/0693 604/167.04 |
| 6,083,194 A | * | 7/2000 | Lopez | A61M 39/02 600/573 |
| 6,142,446 A | | 11/2000 | Leinsing | |
| 7,520,489 B2 | * | 4/2009 | Ruschke | A61M 39/26 251/149.1 |
| 7,670,322 B2 | * | 3/2010 | Fangrow, Jr. | A61M 39/24 604/247 |
| 2006/0264854 A1 | * | 11/2006 | Fangrow | A61M 39/24 604/284 |
| 2011/0049508 A1 | * | 3/2011 | Kawamura | H01L 29/7869 257/43 |

\* cited by examiner

SMART CHECK VALVE

TECHNICAL FIELD

The present disclosure generally relates to a check valve, and more particularly to a check valve integrated with a Y connector.

BACKGROUND

An infusion set has a primary container fluid path from the primary container, and may be attached to an infusion pump. The infusion pump may normally operate in a forward direction to pump fluid from the primary container along the primary fluid path. However, in certain instances it is desirable for the pump to operate in a reverse direction. An occlusion may occur along the fluid path downstream of the infusion pump, such as in part of a tubing downstream of the infusion pump. Depending on the elasticity of the tubing, a significant amount of fluid may accumulate in the tubing. When the occlusion is removed, the stored fluid may be immediately released downstream creating an unintended bolus. Upon detecting the occlusion, the infusion pump may operate in a reverse direction to prevent such an unintended bolus release.

The infusion set may also require connection of a secondary container. A Y connector allows connection of the secondary container. The Y connector may follow a check valve in the primary container fluid path. The check valve prevents the flow of fluid from the secondary container, which may be elevated, into the primary container. In a clinical care setting a Y site is often attached to the infusion set even when no secondary container is attached to the infusion set in order to enable a clinician to attach a secondary container to the infusion set if needed. An infusion set with a Y site connector but without a secondary container attached prevents fluid from flowing in a bi-direction path and only permits fluid to flow from the primary container in a forward direction. In this set-up the conventional check valve may prevent reverse flow even if the secondary container is not attached, and the infusion pump may not operate in the reverse direction. Accordingly, there is a need for an improved Y site check valve system that will enable bi-direction flow of fluid even when a secondary container is not attached.

SUMMARY

Aspects of the subject technology relate to check valves for use with infusion devices and methods of using the same. In accordance with certain aspects, a connector valve comprises a body defining a chamber and comprising a primary inlet, a secondary inlet, and an outlet. The connector valve also comprises a compressible member disposed within the chamber and configured to compress from an uncompressed state to a compressed state. The connector valve also comprises a resilient member disposed within the chamber and engaged with the compressible member such that the resilient member moves within the chamber from an open configuration, when the compressible member is in the uncompressed state, to an occluding configuration, when the compressible member is in the compressed state. The resilient member in the open configuration permits a bidirectional primary fluid flow between the primary inlet and the outlet. The resilient member in the occluding configuration permits a bidirectional secondary fluid flow between the secondary inlet and the outlet, and unidirectional primary fluid flow from the primary inlet to the outlet.

In accordance with certain aspects, a connector valve is disclosed. The connector valve comprises a body defining a chamber and comprising a primary inlet, a secondary inlet, and an outlet. The connector valve also comprises a compressible member disposed within the chamber. The compressible member comprises a first portion connected to a second portion that is compressible. The second portion is configured to compress from an uncompressed state to a compressed state such that the first portion moves axially within the chamber. The connector valve also comprises a valve member disposed around the first portion within the chamber and configured to move axially with the first portion. The valve member obstructs the primary inlet when the second portion is in the compressed state and does not obstruct the primary inlet when the second portion is in the uncompressed state.

In accordance with certain aspects, a connector valve is disclosed. The connector valve comprises a body defining a chamber. The body comprises a first end and a second end, an axis from the first end to the second end, an aperture at the first end, an orifice at the second end defining an outlet, and an opening in the chamber between the first end and the second end and defining a primary inlet. The connector valve also comprises a cap portion connected to the first end of the body and defining an inlet channel connected to the aperture defining a secondary inlet. The connector valve also comprises a check valve member disposed within the chamber. The check valve member comprises an axial portion having a head portion extending between the first end and the second end parallel to the axis. The head portion is configured to engage with the inlet channel when the axial portion is in a first state, and the head portion is configured to disengage from the inlet channel when the axial portion is in a second state. The check valve member also comprises a radial portion extending radially from the axis to the chamber. The radial portion is configured to uncover the opening when the axial portion is in the first state, and the radial portion is configured to cover the opening when the axial portion is in the second state.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
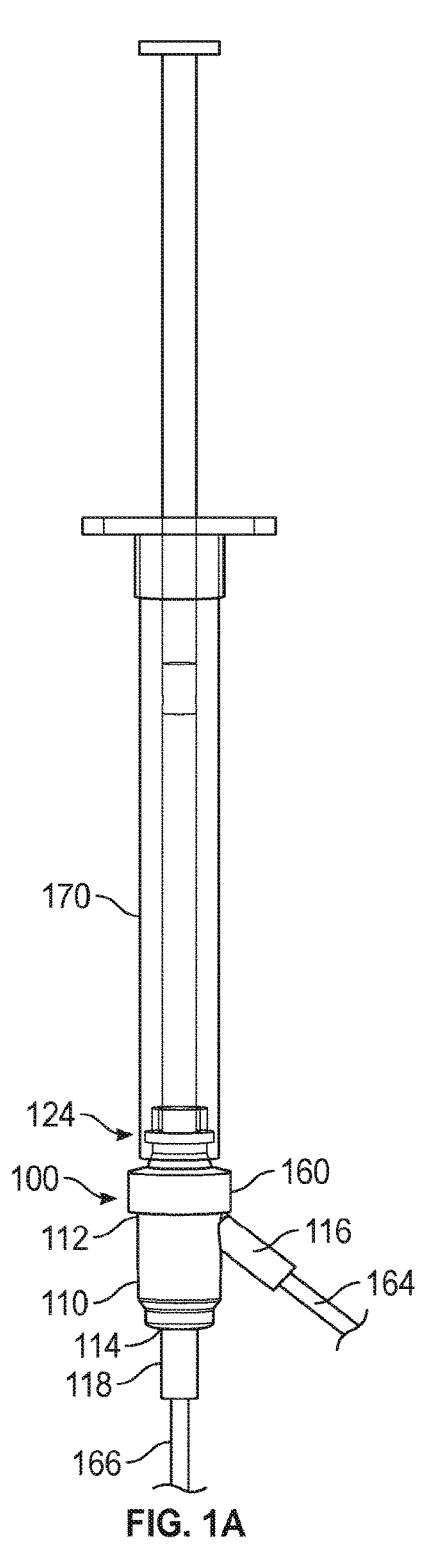
FIG. 1A illustrates an example of a smart check valve, in accordance with aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components may be shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

FIGS. 1A-1D illustrate a smart check valve or connector valve 100, in accordance with aspects of the present disclosure. The connector valve 100 comprises a body 110 and a cap portion 160. The body 110 comprises a first end 112, a second end 114, a primary inlet 116, a secondary inlet 124, and an outlet 118. The body 110 houses a check valve member 180 comprising a compressible member 130 and a valve member or resilient member 150. The cap portion 160 at least partially defines the secondary inlet 124. A syringe 170, for example, is connected to the secondary inlet 124. A primary tubing 164 is connected to the primary inlet 116, and an outlet tubing 166 is connected to the outlet 118. The primary tubing 164 may be connected to a primary container (not shown) such as a bag or other reservoir for holding fluid. The outlet tubing 166 may be connected to a patient or infusion devices connected to the patient.

Figure 1B:
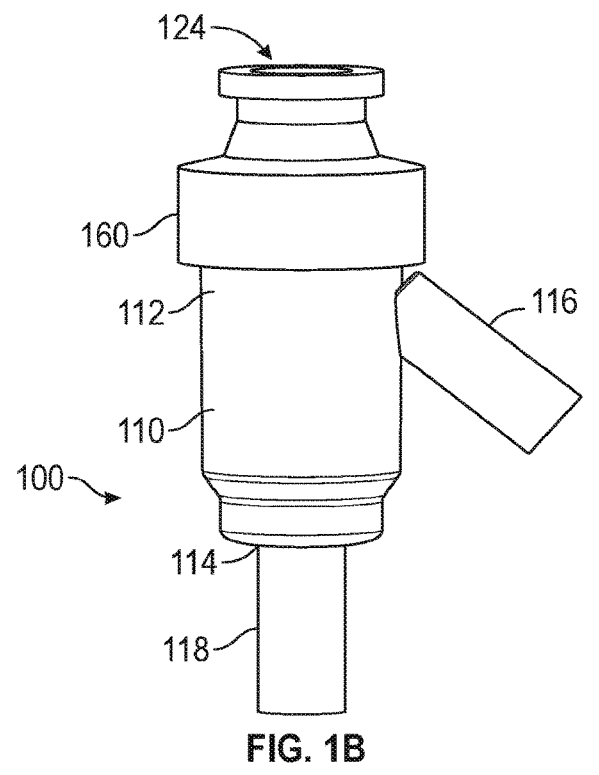
FIG. 1B illustrates the smart check valve of FIG. 1A without connections, in accordance with aspects of the present disclosure.
Figure 1C:
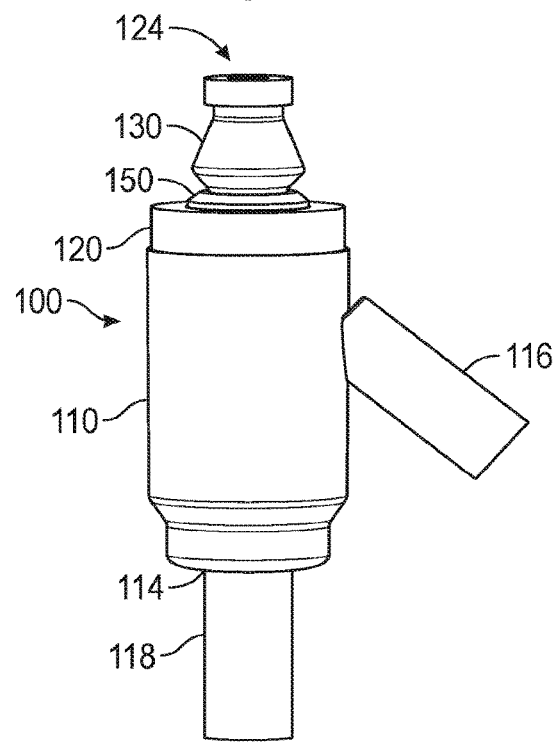
FIG. 1C illustrates the smart check valve of FIG. 1A without a cap portion, in accordance with aspects of the present disclosure.
Figure 1D:
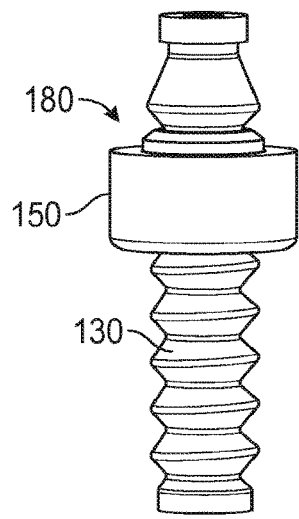
FIG. 1D illustrates internal components of the smart check valve of FIG. 1A, in accordance with aspects of the present disclosure.

FIG. 1B shows the connector valve 100 without any connections. FIG. 1C shows the connector valve 100 without the cap portions 160, illustrating the check valve member 180 disposed within the body 110. FIG. 1D shows the check valve member 180 comprising the compressible member 130 and the resilient member 150. In alternative implementations, the check valve member 180 may comprises a single piece.

The connector valve 100 integrates a Y connector with a check valve that is enabled upon mechanical connection of a secondary container, such as the syringe 170. The secondary container is not limited to syringes and may include a bag or other reservoir. A forward primary fluid flow extends from the primary inlet 116 to the outlet 118. A reverse primary fluid flow extends from the outlet 118 to the primary inlet 116. A forward secondary fluid flow extends from the secondary inlet 124 to the outlet 118. A reverse secondary fluid flow extends from the outlet 118 to the secondary inlet 124.

The check valve member 180 is positioned between the primary inlet 116 and the outlet 118. When no secondary container is connected to the secondary inlet 124, the check valve member 180 is disabled such that fluid may flow in either direction, along the forward primary fluid flow or the reverse primary fluid flow. An infusion pump, which may be connected to the outlet tubing 166, can operate in a forward or reverse direction. The forward direction, along the forward primary fluid flow, allows infusion of fluid from a primary container connected to the primary inlet 116 through the primary tubing 164. The reverse direction, along the reverse primary fluid flow, may be used to prevent an unintentional bolus from forming when there is an occlusion in tubing that is downstream of the infusion pump.

When a secondary container is connected to the secondary inlet 124, the check valve member 180 restricts reverse primary fluid flow into the primary inlet 116. A forward secondary fluid flow extends from the secondary inlet 124 to the outlet 118, and a reverse secondary fluid flow extends from the outlet 118 to the secondary inlet 124. When the check valve member 180 is enabled (e.g., when the secondary container is connected to the secondary inlet 124), the forward primary fluid flow, the forward secondary fluid flow, and the reverse secondary fluid flow are permitted to flow, the reverse primary fluid flow is restricted. The infusion pump can therefore operate in forward or reverse; however, in reverse, the fluid will flow along the reverse secondary fluid flow into the secondary inlet 124. The fluid will not flow into the primary inlet 116, which may prevent mixing of fluids in the primary container. Once the secondary container is empty, fluid flow from the primary container can resume without user intervention.

Figure 2A:
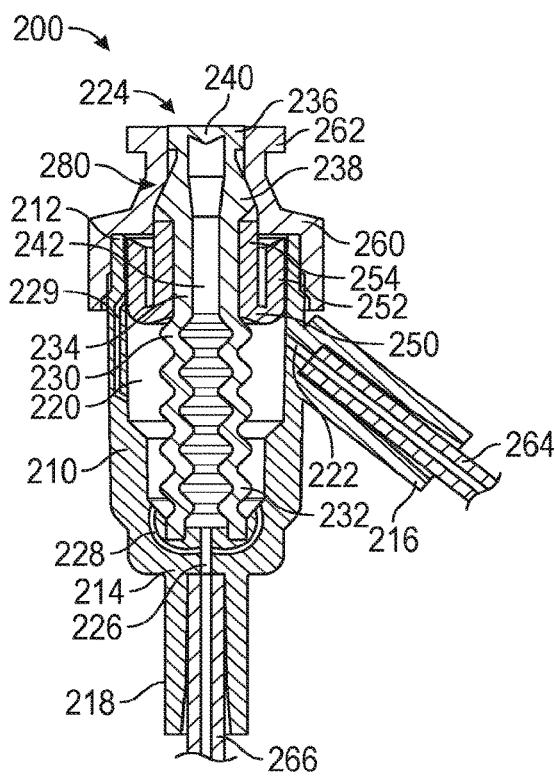
FIG. 2A illustrates a smart check valve without a connection to a secondary container, in accordance with aspects of the present disclosure.
Figure 2B:
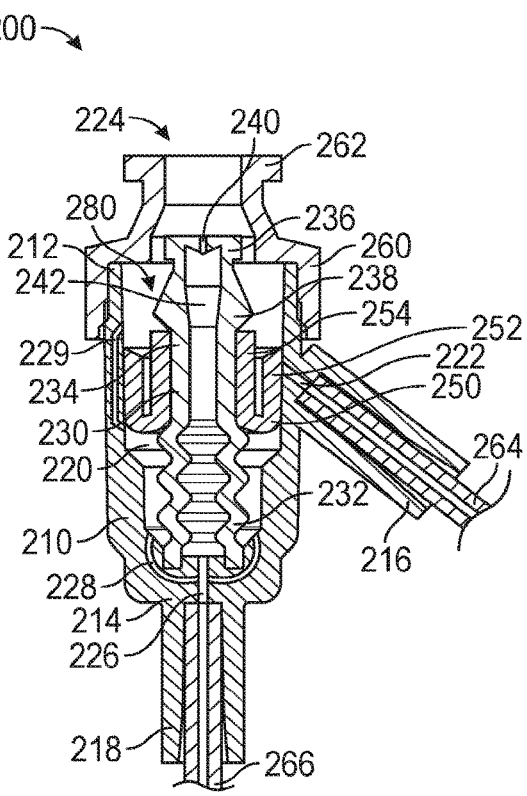
FIG. 2B illustrates the smart check valve of FIG. 2A with a connection to a secondary container, in accordance with aspects of the present disclosure.

Further details and operation of a smart check valve are described with respect to FIGS. 2A and 2B. FIGS. 2A and 2B depict a connector valve 200, which may correspond to the connector valve 100. The connector valve 200 comprises a body 210 and a cap portion 260, which defines a port 262. The body 210 comprises a first end 212, a second end 214, a primary inlet 216, a secondary inlet 224, and an outlet 218. The body 210 houses a check valve member 280 comprising a compressible member 230 and a valve member or resilient member 250. The cap portion 260 at least partially defines the secondary inlet 224. A primary tubing 264 is connected to the primary inlet 216, and an outlet tubing 266 is connected to the outlet 218. The primary tubing 264 may be connected to a primary container (not shown) such as a bag or other reservoir for holding fluid. The outlet tubing 266 may be connected to a patient or infusion devices connected to the patient.

The chamber 220 comprises a plurality of sections, each section having a different radius, wherein the radii diminish from the secondary inlet 224 to the outlet channel 226 such that the radius near the first end 212 is greater than the radius near the second end 214. The sections of the plurality of sections are connected by tapered sections. In other implementations, the chamber 220 may have other shapes, such as a cylindrical shape.

The body 210 defines a first vent 229, a second vent 228, a chamber 220, a primary inlet channel 222, and an outlet channel 226. The first vent 229 forms a fluid flow from an upper portion of the chamber 220 to a lower portion of the chamber 220 and the second vent 228 forms a fluid flow from the lower portion of the chamber 220 to the outlet channel 226. Although FIGS. 2A and 2B show one first vent 229, in other implementations there may be more first vents 229, which may be formed in alternate configurations, such as ridges along the inner sidewall of the body 210. Although FIGS. 2A and 2B show two second vents 228, in other implementations there may be more or less second vents 228, which may be formed in alternate configurations, such as ridges along the inner sidewall of the body 210.

The check valve member 280 comprises an axial portion extending along an axis from the first end 212 to the second end 214. The check valve member 280 also comprises a radial portion extending radially outward from the axis and is configured to form a fluid seal against the chamber 220. The axial portion is configured to move the radial portion within the chamber 220 from a first location, in which the primary inlet channel 222 is exposed, to a second location covering the primary inlet channel 222. The axial portion is configured to keep the radial portion in the first location when there is no connection to the port 262 and to move the radial portion to the second location when a connection to the port 262 is made. In FIGS. 2A and 2B, the compressible member 230 is the axial portion, and the resilient member 250 is the radial portion. In other implementations, the axial portion may comprise a spring-loaded component or other structure capable of moving the radial portion as described herein. In other implementations, the check valve member may comprise a single co-molded piece.

The compressible member 230 comprises a rigid portion 234, a head portion 236, which defines a septum 240, a shoulder portion 238, and a compressible portion 232. The compressible member 230 is preferably hollow, defining an inner channel 242. The head portion 236 is configured to substantially fill the secondary inlet 224 when the compressible member 230 is not compressed. The compressible member 230 is configured to compress when an axial force is applied to the head portion 236 such that the head portion 236 is pushed down and offset from the sealing surface, as seen in FIG. 2B. The septum 240 is configured to open when the head portion 236 is pushed down, permitting flow through the inner channel 242. Although not shown in FIG. 2B, the septum 240 may open enough that the head portion 236 forms a fluid seal against the cap portion 260. The shoulder portion 238 is configured form a fluid seal against an inner surface or sealing surface of the cap portion 260 when the head portion 236 is not pushed down, as seen in FIG. 2A. The rigid portion 234 comprises a cylindrical shape and is configured remain rigid when the head portion 236 is pushed down, as seen in FIG. 2B. The rigid portion 234 is further configured to provide an attachment point for the resilient member 250.

In some implementations, the rigid portion 234 may take on other shapes, such as a box shape. The compressible portion 232 comprises an accordion bellows in FIGS. 2A and 2B and is configured to compress when a load is exerted onto the head portion 236. In other implementations the compressible portion 232 may take on other shapes, such as a notched cylinder (wherein the notches form bending points for compression), or other compressible shapes and forms. Although FIGS. 2A and 2B show the compressible member 230 as a single molded piece, in other implementations the compressible member 230 may comprise separate, joined pieces. The compressible member 230 may be made of a single material or several materials, such as a flexible material for the compressible portion 232 and a harder and stiffer material for the rigid portion 234.

The resilient member 250 comprises a flap 252 and a wall 254. The flap 252 is configured to extend radially outward at a radius substantially similar to a radius of the chamber 220 to contact the inner sidewall of the chamber 220. The chamber 220 may have sections with different radii, such that the resilient member 250 cannot be moved into a section of the chamber 220 having a smaller radius that the radius of the flap 252. The flap 252 is made of a resilient material and is configured to bend away from the inner sidewall from a fluid pressure.

For instance, the flap 252 bends away from the primary inlet channel 222 from a fluid pressure from the primary inlet channel 222. The flap 252 is configured not to allow fluid pressure from the chamber 220 to bend the flap 252. The wall 254 is configured to provide a stable attachment and engage the rigid portion 234 such that when the rigid portion 234 moves, the resilient member 250 moves along with the rigid portion 234. The wall 254 has a radius smaller than that of the flap 252, and substantially similar to a radius of the rigid portion 234. Although FIGS. 2A and 2B show a radial or circular configuration of the resilient member 250, in other configurations the resilient member 250 may take on other shapes configured to provide fluid sealing against the chamber 220. The resilient member 250 may be made of a single piece, or several pieces, and may be made of a single resilient member, or each portion may be made of a different material.

A forward primary fluid flow extends from the primary inlet channel 222, optionally through the first vent 229, through the chamber 220 and the second vent 228, and to the outlet channel 226. A reverse primary fluid flow extends from the outlet channel 226, through the second vent 228, and to the primary inlet channel 222. A forward secondary fluid flow extends from the secondary inlet 224, through the inner channel 242, and to the outlet channel 226. A reverse secondary fluid flow extends from the outlet channel 226, through the inner channel 242, and to the secondary inlet 224.

FIG. 2A shows the check valve member 280 in a first configuration, or open configuration. In the open configuration, a syringe or other fluid connection is not connected to the port 262. The compressible portion 232 is in an uncompressed state. In the open configuration, the septum 240 is closed, and the primary inlet channel 222 is exposed and not obstructed by the resilient member 250. Thus, the forward primary fluid flow and the reverse primary fluid flow are open to permit fluid flow, whereas the forward secondary fluid flow and the reverse secondary fluid flow are blocked to restrict fluid flow. In the open configuration, bidirectional primary fluid flow between the primary inlet channel 222 and the outlet channel 226 is permitted.

FIG. 2B shows the check valve member 280 in a second configuration, or occluding configuration. When a syringe or other fluid connection is connected to the port 262, the head portion 236 is pushed down by compressing the compressible member to a compressed state, which opens the septum 240 and moves the resilient member 250 to contact or block the primary inlet channel 222. With the septum 240 open, the forward secondary fluid flow and the reverse secondary fluid flow are open to permit fluid flow. The reverse primary fluid flow is blocked, by at least the resilient member 250, to restrict fluid flow. However, the forward primary fluid flow is open to permit fluid flow. Fluid pressure from the primary inlet channel 222 may push the flap 252 away from the primary inlet channel 222, allowing fluid from the primary inlet channel 222 to enter the upper portion of the chamber 220. The fluid from the primary inlet channel 222 may flow through the first vent 229 to the lower portion of the chamber 220 (bypassing or flowing around the resilient member 250), and flow through the second vent 228 and through the outlet channel 226. As described above, fluid flow may be reversed without mixing fluids into the primary inlet channel 222. In the occluding configuration, bidirectional secondary fluid flow between the secondary inlet 224 and the outlet channel 226 is permitted, and unidirectional primary fluid flow from the primary inlet channel 222 and the outlet channel 226 is permitted.

In alternative implementations, a smart check valve comprises a Y connector with a check valve member which is always operational, but mechanically bypassed until a secondary container is mechanically connected.

It is understood that any specific order or hierarchy of blocks in the processes disclosed is an illustration of example approaches. Based upon design or implementation preferences, it is understood that the specific order or hierarchy of blocks in the processes may be rearranged, or that all illustrated blocks may or may not be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed provide exemplary approaches. Based upon implementation specifics or preferences, it is understood that the specific order or hierarchy of steps, operations or processes may be rearranged. Some of the steps, operations or processes may be performed simultaneously and some may be omitted. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way.

What is claimed is:

1. A connector valve comprising:
a body defining a chamber and comprising a primary inlet, a secondary inlet, and an outlet;
a compressible member disposed within the chamber and configured to compress from an uncompressed state to a compressed state; and
a resilient member disposed within the chamber and engaged with the compressible member such that the resilient member moves within the chamber from an open configuration, when the compressible member is in the uncompressed state, to an occluding configuration, when the compressible member is in the compressed state; wherein the resilient member in the open configuration permits a bidirectional primary fluid flow between the primary inlet and the outlet, and the resilient member in the occluding configuration permits a bidirectional secondary fluid flow between the secondary inlet and the outlet, and unidirectional primary fluid flow from the primary inlet to the outlet.

2. The connector valve of claim 1, wherein the resilient member obstructs the primary inlet when the resilient member is in the occluding configuration and the resilient member does not obstruct the primary inlet when the resilient member is in the open configuration.

3. The connector valve of claim 1, wherein the compressible member comprises a rigid portion configured to engage the resilient member and a compressible portion configured to compress.

4. The connector valve of claim 1, wherein the compressible member comprises a head portion and a shoulder portion.

5. The connector valve of claim 4, wherein the secondary inlet comprises a secondary inlet opening and a sealing surface, the head portion configured to substantially fill the secondary inlet opening when the compressible member is in the uncompressed state, and the shoulder portion configured to contact the sealing surface when the compressible member is in the uncompressed state to restrict fluid flow through the secondary inlet.

6. The connector valve of claim 5, wherein the head portion is offset from the secondary inlet opening into the chamber when the compressible member is in the compressed state, and the shoulder portion is offset from the sealing surface when the compressible member is in the compressed state to permit fluid flow through the secondary inlet.

7. The connector valve of claim 1, wherein the resilient member extends radially to contact an inner surface of the chamber.

8. The connector valve of claim 7, wherein the inner surface defines an opening for the primary inlet, and the resilient member contacts the inner surface around the opening when the resilient member is in the occluding configuration.

9. The connector valve of claim 8, wherein the resilient member is configured to bend away from the inner surface from a fluid pressure from the primary inlet to permit fluid flow from the primary inlet into the chamber.

10. A connector valve comprising:
a body defining a chamber and comprising a primary inlet, a secondary inlet, and an outlet;
a compressible member disposed within the chamber and comprising a first portion connected to a second portion that is compressible, the second portion configured to compress from an uncompressed state to a compressed state such that the first portion moves axially within the chamber; and
a valve member disposed around the first portion within the chamber and configured to move axially with the first portion,
wherein the valve member obstructs the primary inlet when the second portion is in the compressed state and does not obstruct the primary inlet when the second portion is in the uncompressed state.

11. The connector valve of claim 10, wherein the compressible member is hollow.

12. The connector valve of claim 11, wherein the compressible member permits fluid flow from the secondary inlet, through the compressible member, and to the outlet when the second portion is in the compressed state.

13. The connector valve of claim 10, wherein the second portion of the compressible member comprises an accordion bellow.

14. The connector valve of claim 10, wherein the valve member comprises a wall configured to engage the compressible member, and a flap connected to the wall and configured to obstruct the primary inlet when the second portion of the compressible member is in the compressed state.

15. The connector valve of claim 14, wherein the flap is configured to permit fluid flow from the primary inlet when the second portion of the compressible member is in the compressed state.

16. The connector valve of claim 15, wherein the flap is made of a resilient material, the flap configured to bend away from the primary inlet from a fluid pressure from the primary inlet.

17. The connector valve of claim 10, wherein an axial force against the first portion of the compressible member compresses the second portion of the compressible member.

18. A connector valve comprising:
a body defining a chamber and comprising:
a first end and a second end;
an axis from the first end to the second end;
an aperture at the first end;
an orifice at the second end defining an outlet; and
an opening in the chamber between the first end and the second end and defining a primary inlet;
a cap portion connected to the first end of the body and defining an inlet channel connected to the aperture defining a secondary inlet; and
a check valve member disposed within the chamber and comprising:
an axial portion having a head portion extending between the first end and the second end parallel to the axis, the head portion configured to engage with the inlet channel when the axial portion is in a first state, the head portion configured to disengage from the inlet channel when the axial portion is in a second state; and
a radial portion extending radially from the axis to the chamber, the radial portion configured to uncover the opening when the axial portion is in the first state, the radial portion configured to cover the opening when the axial portion is in the second state.

19. The connector valve of claim 18, wherein the axial portion and the radial portion are co-molded.

20. The connector valve of claim 18, wherein the chamber comprises a plurality of sections, each of the sections having a respective radius.

21. The connector valve of claim 20, wherein each respective radius is different.

22. The connector valve of claim 20, wherein a radius near the first end is greater than a radius near the second end.

23. The connector valve of claim 20, wherein the plurality of sections are connected by a plurality of tapered sections.

24. The connector valve of claim 20, wherein the radial portion comprises a wall portion having a first radius and a flap portion having a second radius, the second radius greater than the first radius, the second radius substantially similar to a radius of one of the plurality of sections near the first end.

25. The connector valve of claim 24, wherein an aperture radius of the aperture is substantially similar to the second radius of the radial portion.

26. The connector valve of claim 18, wherein the cap portion defines a secondary inlet port configured to receive a secondary connection tip.

27. The connector valve of claim 26, wherein the secondary connection tip is configured to apply an axial force against the head portion of the check valve member in the second state.

28. The connector valve of claim 18, wherein the outlet is configured to couple to an infusion pump.

\* \* \* \* \*